(12) United States Patent
Moulin et al.

(10) Patent No.: US 9,324,079 B2
(45) Date of Patent: Apr. 26, 2016

(54) SYSTEM AND POUCH WITH QR CODE, RFID TAG, AND/OR NFC TAG

(71) Applicants: iZipline LLC, Sarasota, FL (US); Pouch Pac Innovations, LLC, Sarasota, FL (US)

(72) Inventors: Michelle A. Moulin, Sarasota, FL (US); Troy Pittman, Sarasota, FL (US); R. Charles Murray, Sarasota, FL (US)

(73) Assignee: iZipline LLC, Sarasota, FL (US)

( * ) Notice: Subject to any disclaimer, the term of this patent is extended or adjusted under 35 U.S.C. 154(b) by 107 days.

(21) Appl. No.: 14/206,255

(22) Filed: Mar. 12, 2014

(65) Prior Publication Data

US 2014/0266626 A1   Sep. 18, 2014

Related U.S. Application Data

(60) Provisional application No. 61/777,862, filed on Mar. 12, 2013.

(51) Int. Cl.
  *G06Q 30/00* (2012.01)
  *G06F 19/00* (2011.01)
  *G06K 7/10* (2006.01)

(52) U.S. Cl.
  CPC ............ *G06Q 30/00* (2013.01); *G06F 19/3456* (2013.01); *G06K 7/10366* (2013.01)

(58) Field of Classification Search
  CPC . G06K 7/10366; G06F 19/3456; G06Q 30/00
  USPC ......................................................... 340/10.1
  See application file for complete search history.

(56) References Cited

U.S. PATENT DOCUMENTS

| | | | |
|---|---|---|---|
| 2007/0210164 A1 | 9/2007 | Conlon et al. | |
| 2008/0132167 A1* | 6/2008 | Bent et al. | 455/41.2 |
| 2008/0186188 A1* | 8/2008 | Chang | 340/572.8 |
| 2009/0226605 A1* | 9/2009 | Chopra et al. | 427/125 |
| 2010/0174599 A1* | 7/2010 | Rosenblatt et al. | 705/14.37 |
| 2010/0294835 A1* | 11/2010 | Bam et al. | 235/382 |
| 2011/0050426 A1 | 3/2011 | Choong | |
| 2013/0059534 A1* | 3/2013 | Sobalvarro et al. | 455/41.1 |

\* cited by examiner

*Primary Examiner* — Jennifer Mehmood
*Assistant Examiner* — Omar Casillashernandez
(74) *Attorney, Agent, or Firm* — Dinsmore & Shohl LLP

(57) ABSTRACT

A system for obtaining information from a flexible pouch having an information tag is provided. The system has a management platform, a brand/tag manager and a communication network that affords for an individual using a personal electronic device (PED) to interact with content related to the flexible pouch and/or product within the flexible pouch. The system also includes on-the-fly coding of the information tag as it is printed onto a flexible pouch, the on-the-fly coding being a function and/or analysis of past interactions by individuals viewing, purchasing and/or using flexible pouches with information tags.

18 Claims, 5 Drawing Sheets

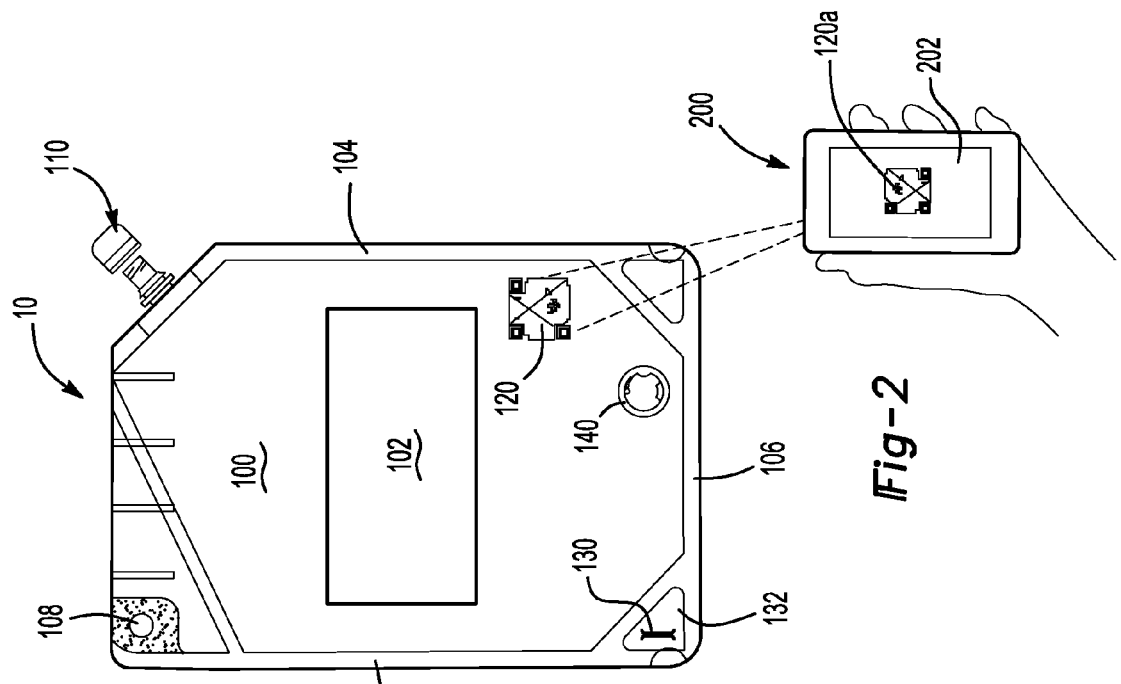
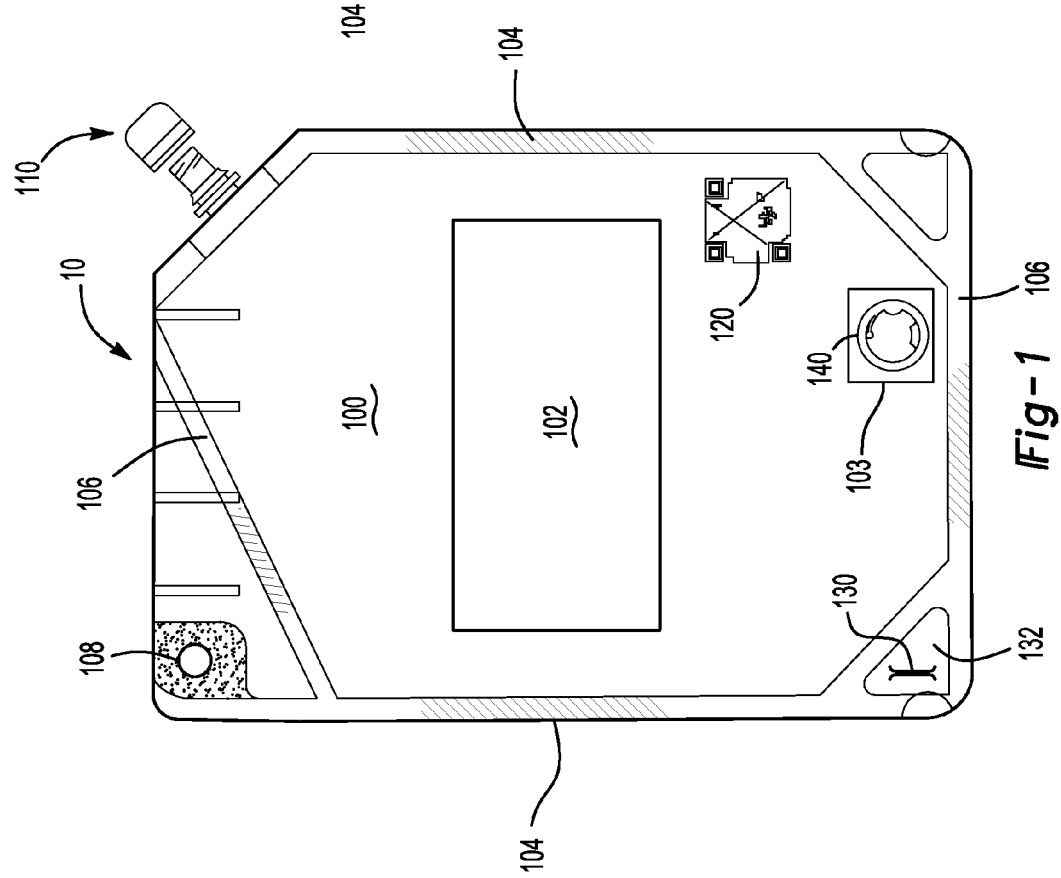

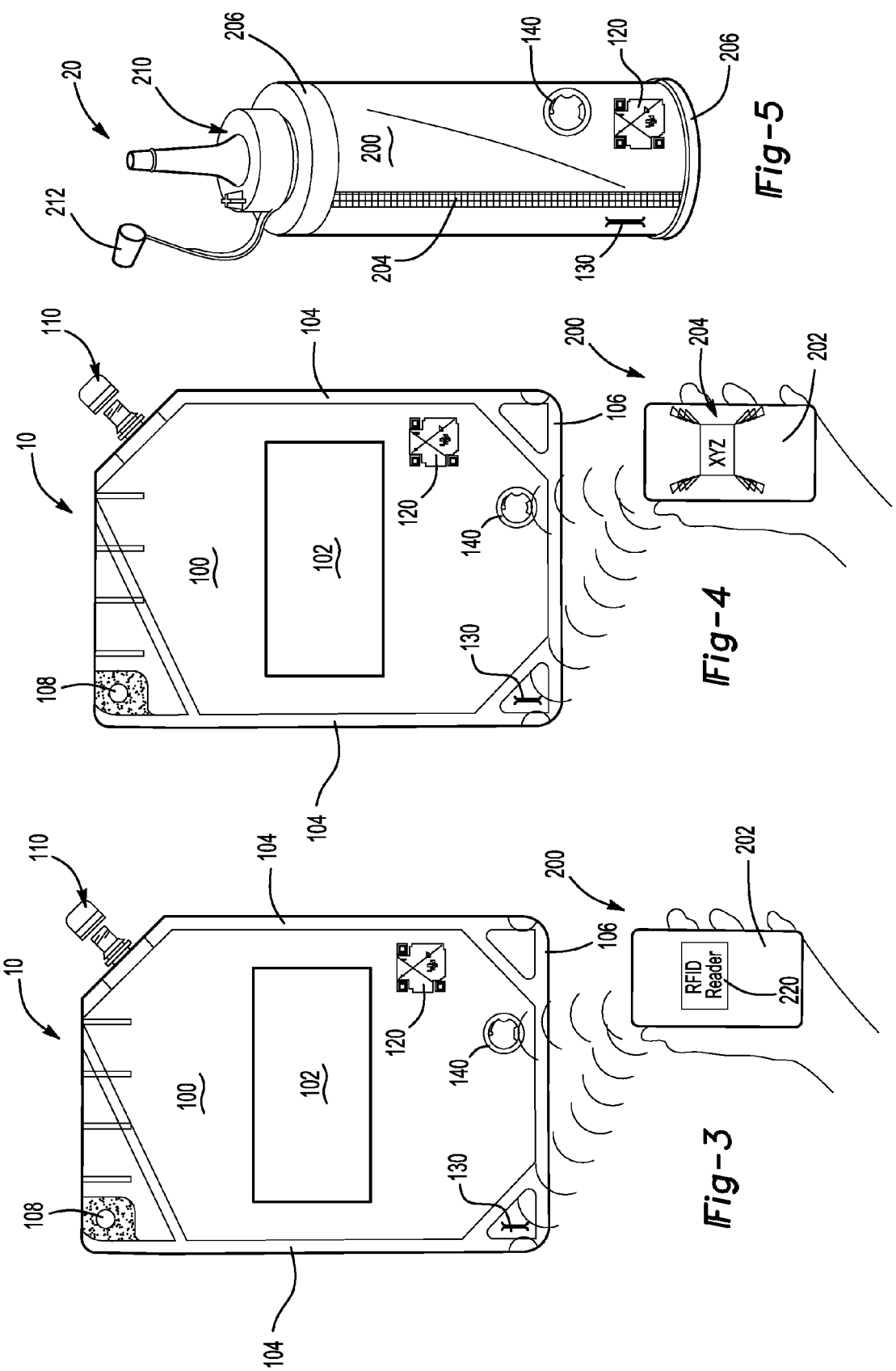

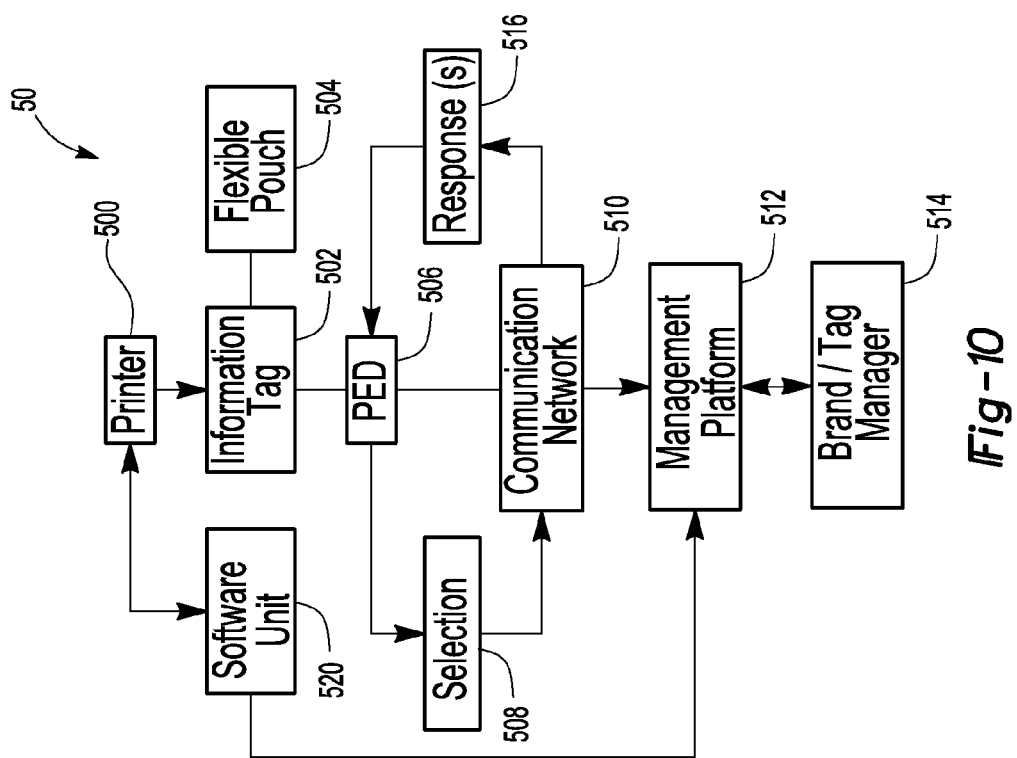
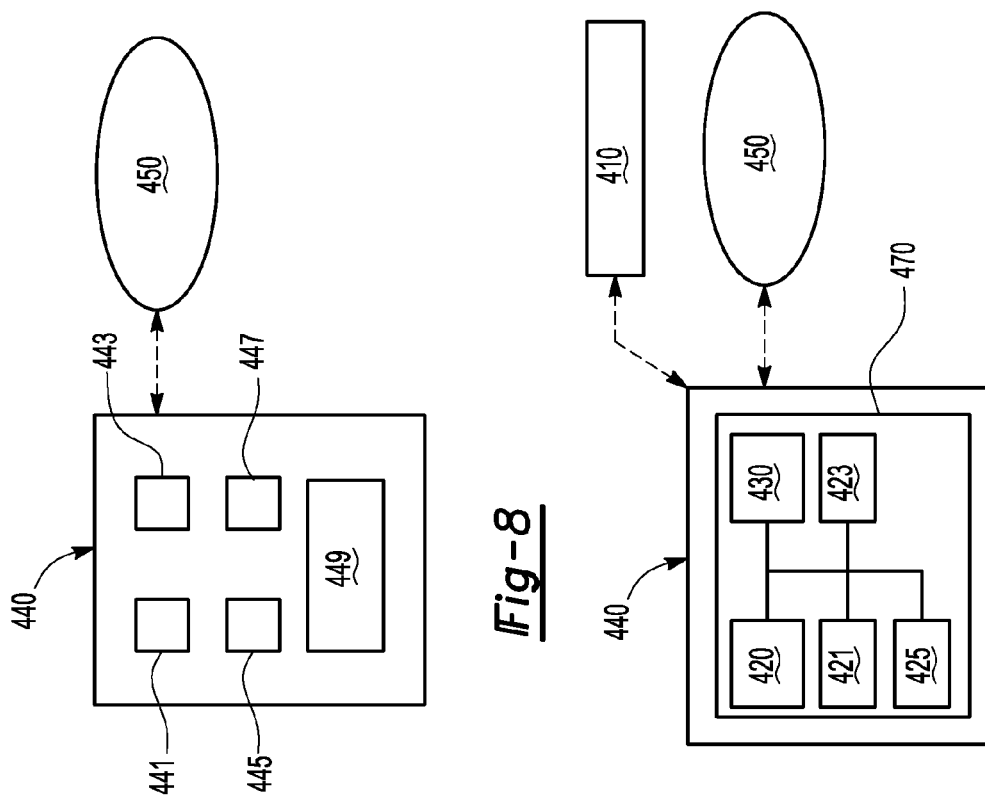

SYSTEM AND POUCH WITH QR CODE, RFID TAG, AND/OR NFC TAG

CROSS-REFERENCE TO RELATED APPLICATIONS

This application claims priority of U.S. Provisional Patent Application 61/777,862 filed Mar. 12, 2013, which is included in its entirety herein by reference.

FIELD OF THE INVENTION

The present invention is related to a system for obtaining information from flexible pouches, and in particular, to such a system that includes a communication network, a management platform, and a brand/tag manager in communication with a flexible pouch having an information tag.

BACKGROUND OF THE INVENTION

Flexible pouches are known for containing a liquid, powder material, and the like. Such pouches are also known to have bar codes, quick response (QR) Codes and/or radio frequency identification (RFID) tags attached thereto such that information on the pouch and/or material contained within the pouch are provided at a desired time. However, both bar codes and RFID tags typically require a special electronic scanner or reader to obtain such information. Therefore, a flexible pouch that can provide desired information to a portable electronic device would be desirable. A system that can provide flexible pouch and/or product information to a portable electronic device used by an individual to scan or read a bar code, QR code and/or RFID tag on a pouch would also be desirable.

SUMMARY OF THE INVENTION

A flexible pouch having an information tag such as a bar code, QR (Quick Response) code, an RFID (Radio Frequency Identification) tag and/or an NFC (Near Field Communication) tag attached thereto is provided. The bar code, QR code, RFID tag and/or NFC tag has, provides and directs a portable electronic device (PED) to a specific URL (Uniform Resource Locator). Naturally, the specific URL links to a website, webpage and the like, which subsequently provides data, information, etc., back to the PED. It is appreciated that a PED can be a smartphone, tablet, laptop and the like, or in the alternative, any new type of PED not yet known to those skilled in the art but operable to be easily carried by an individual and communicate with a communication network such as a wireless telephone network, the internet and the like.

A system for providing the bar code, QR code, RFID tag and/or NFC tag and for providing pouch and/or product information to the PED is also provided. The system has a management platform, a brand/tag manager and a communication network that affords for an individual using the PED to interact and engage with desired content related to the pouch and/or product for a bar code, QR code, RFID tag and/or NFC tag that has been scanned or read by the PED. In addition, the system affords for businesses such as retailers, marketing companies, etc., to interact with the individual using the PED. In this manner, enhanced or "rich" pouch and/or production information can be provided to the individual using the PED.

The management platform and brand/tag manager responds to information read from the information tag and provided by the PED with at least one response. The at least one response can be a sales coupon, an advertisement, a question, a link to an electronic game, an electronic game download, a photograph, a song, and the like. In addition, the management platform provides the at least one response to the PED via the communication network. In some instances, the brand/tag manager provides the response.

The PED is operable to receive the response and generate a reply provided by a user and communicate the reply to the management platform and/or the brand/tag manager via the communication network. Upon receiving the reply, the management platform can execute an analysis thereof and modify future responses as a function of the analysis.

It is appreciated that the information tag has an antenna printed onto the flexible pouch and the antenna is printed using an information tag printer that may or may not contain or use ink that has conductive nanoparticles. In addition, a software unit, module, program, etc., can be provided which is operable to code the information tag with the at least one type of information during printing of the information tag. The software unit may or may not be located on a flexible pouch manufacturing machine and/or the information tag printer.

BRIEF DESCRIPTION OF THE DRAWINGS

FIG. 1 is a schematic illustration of a flexible pouch having a QR code, an RFID tag and/or an NFC tag according to an embodiment of the present invention;

FIG. 2 is a schematic illustration of a portable electronic device (PED) that is scanning, reading, and/or imaging the QR code shown in FIG. 1;

FIG. 3 is a schematic illustration of the PED shown in FIG. 2 having an RFID and/or NFC tag reader that has been activated and is sending a signal to the RFID tag and/or NFC tag shown in FIG. 1;

FIG. 4 is a schematic illustration of the RFID tag and/or NFC tag shown in FIG. 3 communicating or transmitting a signal to the PED;

FIG. 5 is a schematic illustration of another flexible pouch having a bar code, QR code, RFID tag and/or NFC tag according to an embodiment of the present invention;

FIG. 8 is a schematic illustration of various PED components used according to an embodiment of the present invention;

FIG. 9 is a schematic illustration of a management platform according to an embodiment of the present invention;

FIG. 10 is a schematic illustration of a system that prints an information tag on a flexible pouch according to an embodiment of the present invention.

DETAILED DESCRIPTION OF THE INVENTION

Figure 7:
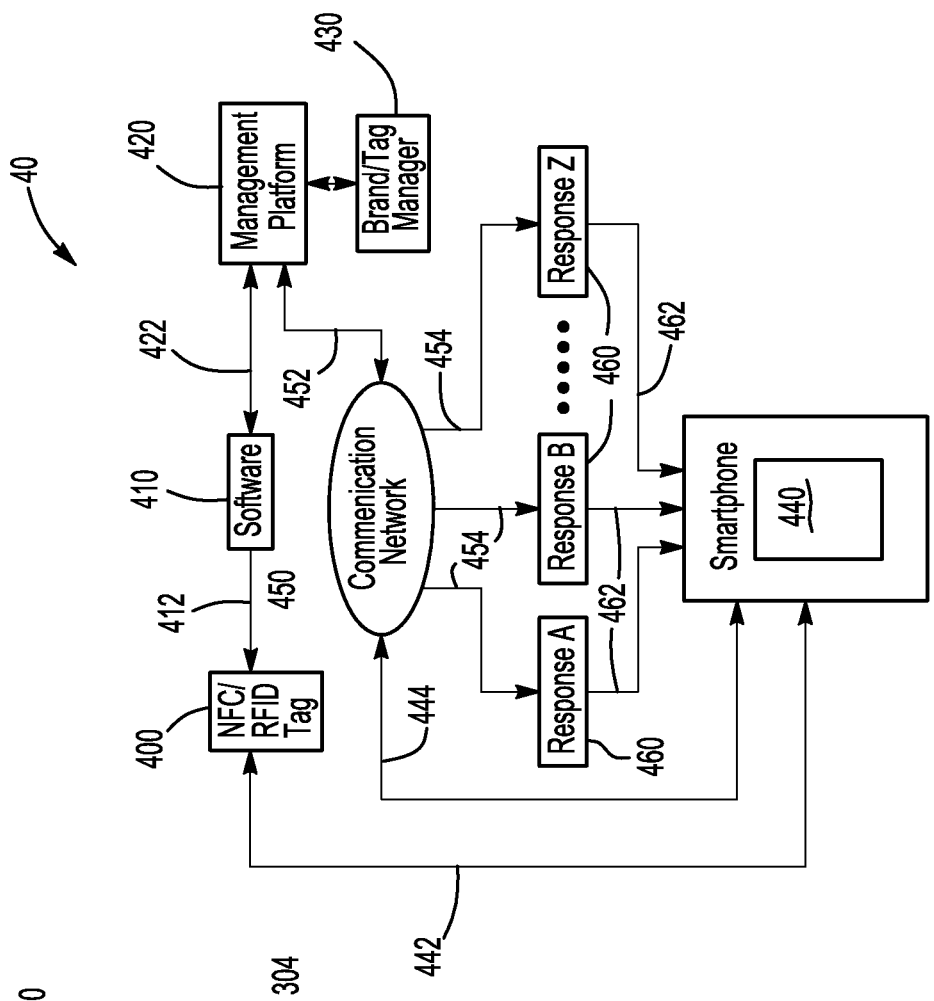
FIG. 7 is a schematic illustration of a system that receives and/or provides information or data to a PED according to an embodiment of the present invention.

A flexible pouch having an information tag such as a QR code, an RFID tag, and/or an NFC tag attached thereto is provided. In addition, a system that affords for scanning/reading of the QR code, RFID tag, and/or NFC tag is included, the system also being operable to receive pouch and/or product information from the information tag and provide a response to the information.

The system includes a PED, a communication network, a management platform, and a brand/tag manager. In combination with the information tag associated with a particular flexible pouch, the system can provide specific information as a function of location of the pouch, a product contained within the pouch, and the pouch itself. In some instances, the information tag is an NFC tag, and the NFC tag can in fact be an RFID tag, a modified RFID tag and the like.

In one embodiment, the PED is used to scan or read a QR code on a flexible pouch container, the QR code providing a URL to the PED which subsequently connects with a website or webpage associated with the URL. In this manner, information such as advertising, discount coupons, etc. for the flexible pouch and/or a product contained within the flexible pouch which the QR code is attached thereto can be provided to an individual that has the PED, e.g. a PED.

In another embodiment, the PED can communicate with an RFID and/or NFC tag which directs the PED to a management platform. For the purposes of the present invention, the term management platform refers to a software and/or hardware system that receives and sends information related to a scanned or read RFID and/or NFC tag. Upon receiving contact from the PED, the management platform provides product and/or pouch information back thereto. In some instances, the PED communicates a current geographical location and/or a preferred language to the management platform. Then in return, the management platform provides information related to the location and/or preferred language back to the PED. For example, if the location is determined to be a retail location, e.g. a clothing store, a grocery store, restaurant, etc., the management platform can provide information such as a discount coupon, recipes, other products to be purchased with the given flexible pouch and the like. In the alternative, if the location is determined to not be a retail location, e.g. a residence for an individual, the management platform realizing that the flexible pouch is at a residence can provide cooking instructions, storage instructions, etc., for a product within the flexible pouch.

Regarding a preferred language, if the language of use for the PED is English, Spanish, French, etc., then information or data from the management platform can be provided back to the PED in English, Spanish, French, etc., respectively.

The system can also provide a response to the PED based on past, present and/or continuing evaluation of actions or selections received by the management platform. For example and for illustrative purposes only—and in response to receiving a URL from a PED that has scanned or read a bar code, QR code, RFID tag and/or NFC tag—the management platform can provide at least two responses, e.g. two choices, for an individual using the PED to select from. In addition, based on a past, present and/or ongoing analysis of selections by a plurality of individuals that have scanned similar pouches providing the same URL, the system can provide only one of the choices to the PED. In the alternative, the system can alter the order of presenting the choices to the PED. In another alternative, the system can provide additional choices to the PED. The choice(s) provided to the PED can also be determined by one or more events, locations, etc. that may affect an individual's purchasing behavior.

Turning now to FIG. 1, an embodiment of a pouch according to an embodiment of the present invention is shown generally at reference numeral 10. The pouch 10 can have a side panel 100, at least one side seam 104, and one or more end seams 106. The pouch may or may not have a label 102, an aperture 108 for hanging the pouch, and/or a fitment 110 for removal of a product contained within the pouch 10.

The pouch 10 has a bar code (not shown), QR code 120, RFID tag 130 and/or NFC tag 140. The RFID tag 130 and/or NFC tag 140 can be attached to a surface of the pouch 10 and may or not be laminated, i.e. be located between a side panel 100 and an overlying laminate layer. In the alternative, the RFID tag 130 and/or NFC tag 140 can be attached or printed to the side panel 100 using an adhesive or ink, or placed and located within the pouch 10. It is appreciated that the RFID tag 130 and/or NFC tag 140 can be located within an air pocket 132, the air pocket 132 affording better reception to and transmission from the RFID tag 130 and/or NFC tag 140. In addition, if the RFID tag 130 and/or NFC tag 140 is printed and/or placed onto a flexible pouch having a foil layer that is at least part of the side panel 100, an insulating layer 103 can be present between the RFID tag 130 and/or NFC tag 140 and the side panel 100. In this manner, the tag can be insulated from the foil layer and improved communication with the tag is afforded. Also, the insulating layer 103 can be made from any insulting material known to those skilled in the art, illustratively including an electrically insulting tape layer, electrically insulting paint layer, electrically insulting paper layer and/or electrically insulting polymer layer.

In addition to the above, an antenna of the RFID tag 130 and/or NFC tag 140 is printed on the pouch 10 using an ink with nanoparticles. The shape of the antenna may or may not be in the form of a plurality of concentric circles as illustrated by the general shape of the NFC tag 140 in FIG. 1. After the printer has finished printing the antenna, the last printed portion of the antenna can still be "wet", i.e. not yet completely solid, and a microchip is placed onto the ink with an electrical connection thus made. In some instances, the newly placed microchip is exposed to a flash of light to enhance drying of the ink and reaction of the ink with the microchip to produce a fused metal contact therebetween and thereby afford for the microchip to send and/or receive signals via the antenna.

In the alternative, the printing, placing of the microchip and optional flashing of light described above can be performed on a separate material, e.g. a sheet of paper, plastic, etc., which is subsequently attached or placed within the flexible pouch 10.

In some instances, a chipless or IC-less NFC tag as is known to those skilled in the art is printed onto and/or placed within the flexible pouch 10. The chipless or IC-less tag can be printed with printed dopant layers and materials such as disclosed in U.S. Pat. Nos. 7,767,520; 7,977,240; 8,066,805; 8,191,018; 8,227,320; and 8,304,780, all of which are incorporated herein in their entirety by reference.

Turning now to FIG. 2, a PED 200 having a screen 202 and a QR code reader 120a scans or reads the QR code 120 as is known to those skilled in the art. For example, applications can be downloaded or installed onto the PED 200 that afford for scanning and recognizing QR codes. Also, QR codes can provide information such as a website address (URL) to the PED and the PED can then be directed to the website, webpage, etc. associated with the particle URL provided by the QR code.

In the alternative, FIG. 3 illustrates the PED 200 with an RFID and/or NFC tag reader 220 (hereafter referred to simply as a "reader") transmitting a signal to the RFID tag 130 and/or that NFC tag 140. For example, if the RFID tag 130 and/or NFC tag 140 is a passive RFID tag and/or passive NFC tag, then a signal from the reader 220 is required. However it is appreciated that if the RFID tag 130 and/or NFC tag 140 is an active tag, then the reader 220 can simply receive a signal from the RFID or NFC tag, i.e. a signal from the reader 220 is not required.

Assuming the RFID tag 130 and/or NFC tag 140 is a passive tag, and upon activation of the RFID tag 130 and/or NFC tag 140 by the signal from the RFID reader and/or NFC chip 220, the RFID tag 130 and/or NFC tag 140 provides a signal to the reader 220 as illustrated in FIG. 4, which may or may not be converted and/or displayed as information 204 on the screen 202. For example, the information 204 can be in the form of specific URL and/or a specific URL plus tag identifier associated with the pouch 10. In the alternative, information 204 can include any kind of information related to the flexible pouch 10 and/or material contained within the pouch 10 as is known to those skilled in the art. For example and for illustrative purposes only, the signal from the RFID tag 130 and/or NFC tag 140 can provide information such as an expiration date of material contained within the pouch 10; nutritional information such as calories, grams of protein, grams of carbohydrate, grams of fat, etc. for a product contained within the pouch; marketing information on material contained within the pouch 10; marketing information on the pouch itself; age restrictions on individuals that may or may not purchase the product; product recall notice information; medication dosage information, medication indications/contraindications information; and the like. It is appreciated that the term indication refers to valid reason to use a certain medical test or medication and the term contraindication refers to a condition or factor that serves as a reason to withhold a certain test or medication.

In this manner, a customer or an employee at a given location can obtain desired information on a particular flexible pouch and its contents.

Figure 6:
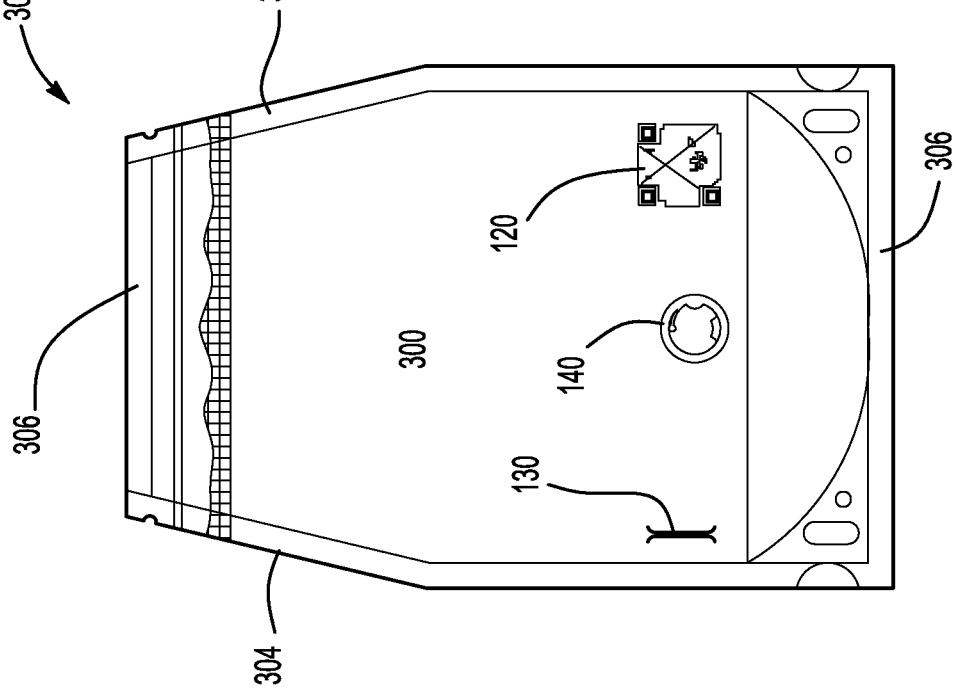
FIG. 6 is a schematic illustration of yet another flexible pouch having a bar code, QR code, RFID tag and/or NFC tag according to an embodiment of the present invention.

Other embodiments of flexible pouches that contain a bar code (not shown), QR code 120, RFID tag 130 and/or NFC tag 140 are shown in FIGS. 5 and 6 at reference numerals 20 and 30, respectively. As shown in FIGS. 5 and 6, a flexible container designed to hold or contain condiments, juices, cereals, adhesives, candy, medical supplies, medication supplies and the like can be included.

The flexible container/pouch can be made from any material known to those skilled in the art such as sheet layer material typically used for flexible pouch manufacture. In addition, the bar code, QR code, RFID tag and/or NFC can be printed onto the surface of the sheet layer material, taped onto the sheet layer material, glued onto the sheet layer material and/or placed within the pouch.

Turning now to FIG. 7, an embodiment of a system to provide information related to a flexible pouch and/or product contained within a flexible pouch is shown generally at reference numeral 40. The system 40 includes an NFC and/or RFID tag 400 associated with a flexible pouch (not shown). The tag 400 can be attached to the flexible pouch, contained within the pouch and the like. In some instances, the tag 400 can be printed onto an inner or outer surface of the pouch.

A software module 410 can be included, the software module 410 operable to code the tag 400. In some instances, the software module 410 codes a plurality of tags "on the fly", i.e. during the manufacture of tags and/or placement of the tags on or in respective pouches. The tags 400 can be coded to contain or have with various types of information such as a URL, a unique identifier for each pouch, a unique identifier for a plurality of pouches fabricated within a given time period and/or date, time and date of manufacture of a pouch, contents within a pouch, a manufacturer of the pouch and/or product contained within the pouch, a product supplier for material used to fabricate the pouch, and the like. In addition, environmental factors associated with the pouch, product contained in the pouch, date and time related to the manufacture of the pouch, date and time product was placed into the pouch, and the like can be coded into or on the tag(s) 400.

The software module 410 can be located on a flexible pouch manufacturing machine (not shown), an RFID and/or NFC tag printer (not shown) and the like. In addition, the software module 410 can be part of an electronic control unit (ECU) and can receive data from any number of sources, illustratively including a flexible pouch manufacturing machine, an RFID and/or NFC tag printer, a pouch material supplier, a supplier of product contained or to be contained within a flexible pouch and the like. Based on the data received from a particular source, the software module 410 can code the RFID and/or NFC tags as a function thereof.

The software 410 can also be in communication with a management platform 420 which is in communication with a brand/tag manager 430. In this manner, data can be provided to the software module 410, e.g. before coding of a plurality of tags 400, and/or the software module 410 can provide data to the management platform and/or brand/tag manager 430, e.g. after coding of a plurality of tags. The NFC and/or RFID tag 400 can be coded via link 412 and the software 410 is in communication with the management platform 420 via link 422. Finally, the management platform 420 is in communication with the brand/tag manager 430 via link 432.

The tag 400 can be encoded with data or information as described above, e.g. with a URL that directs a PED 440 to the management platform 420. In particular, the PED 440 can read the tag 400 using NFC communication as is known to those skilled in the art. Such communication is commonly referred to as "tapping" or being "tapped". Upon tapping the tag 400 with the PED 440 via link 442, a unique URL can appear on the PED 440 via NFC software and components inherent and/or included within the PED 440. The URL is then directed from the PED 440 through a communication network 450 to the management platform 420 via links 444 and 452, respectively.

In some instances, a unique sound can be audibly played by the PED 440 when the URL is directed or transmitted to the communication network 450 and/or management platform 420. The unique sound, e.g. a unique "whoosh" informs a user of the PED 440 that the phone is in communication or attempting to be in communication with the management platform 420.

Upon receiving the unique URL, the management platform 420 recognizes the unique URL code and allocates a predetermined response designed by the brand/tag manager 430 via link 432. In addition, the brand/tag manager 430 can provide response data or information back to the PED 440 via link 432, management platform 420, link 452, communication network 450 and link 444. The data or information from the brand/tag manager 430 can be preassigned responses in the form of a webpage or web application such that a coupon, question, game, survey, photo, and the like is provided to the user operating the PED 440. In some instances, audio can be included with one or more responses.

It is appreciated that the user of the PED 440 can interact with the received data or information, such interaction being transmitted back to the management platform 420 to be analyzed, responded to, stored for later analysis, etc. For example and for illustrative purposes only, FIG. 7 illustrates a series of responses 460 that can be transmitted to the PED 440 via links 462. The responses labeled Response A, Response B, . . . Response Z can originate from the management platform 420 and/or brand/tag manager 430, and be submitted in response to information or data obtained from the NFC and/or RFID tag 400 by the PED 440 and communicated to the management platform 420 via the communication network 450. A user of the PED 440 can select a particular response, e.g. Response B, which affords continued interaction between the user and the system 40. For example and for illustrative purposes only, selection of Response A triggers the management platform 420 and brand/tag manager 430 to deliver a coupon back to the PED 440. Other responses from the management platform 420 and brand/tag manager 430 can include one or more questions delivered to the PED 440, an electronic game or a link to an electronic game to the PED 440, a survey to be completed by the user of the PED 440, a photo, a song, and the like.

The system 40 also affords for analysis of selections to one or more of the responses 460. For example, a plurality of similar coded tags 400 can be scanned by a plurality of PEDs, e.g. by individuals purchasing flexible pouches having a tag 400. In response to the tags 400 being scanned, at least a subset of individuals respond or select one of the responses 460 provided to their PED. In addition, the management platform 420 can store and/or analyze the selections and in return provide only the responses 460 to future users that tap a similar coded NFC and/or RFID tag 400.

The responses 460 can be related to a specific location and/or event that one or more users with the PED(s) 440 are located at and/or participating in. For example, if the user of the PED 440 is at a sporting event and purchases a flexible pouch having the tag 400, a response 460 provided by the management platform 420 and brand tag manager 430 can be specifically oriented or associated with the sporting event. Again, for example and illustrative purposes only, upon tapping of a flexible pouch having a tag 400, the PED 440 can direct a URL of the tag and a GPS location of the PED to the management platform 420. Based on the GPS location, and possibly a date and time of the tapping event, the management platform 420 can determine that the PED and thus the individual are at a known sporting event. Furthermore, the tag 400 can transmit data or information that informs the management platform 420 that a flexible pouch with alcoholic beverage therewithin has been or may be purchased. Finally, such information can be used by the management platform 420 and the brand/tag manager 430 to provide a response 460 in the form of an advertisement for a local entertainment facility such as a bar, restaurant and the like.

The system 40 can also afford for an advertisement and/or opportunity for the user of the PED 440 to purchase an item associated with the sporting event such as a cap, jersey, etc., at the sporting facility and/or online, e.g. over the internet. It should be appreciated that anything on a webpage or web application can be provided to the PED 440 as a result of the phone tapping the tag 400.

The PED 440 can have one or more components as illustrated in FIG. 8. For example, the PED 440 can have a bar code scanner/reader 441, a QR code scanner or reader 443, an RFID tag reader or scanner 445, and/or an NFC tag scanner or reader 447. In addition, the PED 440 can have a software module 449 that communicates with the components 441-447 and directs communication with the communication network 450, management platform 420, and/or brand/tag manager 430.

The management platform 420 can be located on a computer 460 which has a processing unit 470 as illustrated in FIG. 9. The processing unit 470 can include some or all of the management platform 420 and/or the brand/tag manager 430. In some instances, the brand/tag manager 430 is contained in a separate computer, however this is not required. The computer 460, processing unit 470 and/or management platform 420 can include memory 421, a software module 423, and a communication module 425 that are in electronic communication with each other. Also the management platform 420 communicates with the communication network 450 and the software 410.

The software 410 can code the tag 400 in real time, i.e. as the tags are being produced and/or placed within and/or attached to a flexible pouch container. The software 410 can communicate with the management platform 420 and/or brand/tag manager 430 and thus provide data on how many tags 400 have been produced, a product contained within a flexible pouch associated with the tags 400, and the like. In this manner, two-way communication between the software 410 and the brand/tag manager 430 can be obtained.

The system 40 affords for a number of advantages over current art systems. For example and for illustrative purposes only, the system 40 provides a unique numbering system to identify the tags 400; allows for language detection for choice of media/data provided to the PED 440; coupon distribution and/or other brand loyalty actions/responses; analysis of customer responses to data provided to the PED 440; ability for brand protection to reduce counterfeiting through the use of unique code URLs/IDs; tracking the number of clicks from one or more PEDs 440 associated with a particular product; tracking of the number of tags and/or flexible pouches associated with particular tags in the marketplace; added value in the marketplace in the form of software as a service (SAAS); custom analytics and reporting directly to the brand manager's website; mobile landing page generator that may or may not be multilingual; publishing and unpublishing of the tags 400; setting of timing for broadcast frequency and type; bilateral communication between the product/production machinery to the management platform 420; generating and writing of tags 400 while in communication with the management platform 420; and mass coding of tags during assembly line production of the labeling, embedding, placing, and/or printing of the tags 400.

In this manner, a system is provided for enhancing the marketability, sales, and user enjoyment of specific and desired flexible pouches. It should be appreciated that data provided to the PED 440 in the form of a webpage, text, tweet, and the like can include health information; calories; ingredients; how to use or open a flexible pouch; how not to use a flexible pouch; a list of complementary items/products; whether or not the product is organic; the place of origin of the product; related nonprofit/charity organizations associated with the product; a percentage of sale of the product to be donated to a nonprofit/charity organization; links to other products such as movies, documentaries, music videos, music, and the like; links to Twitter accounts; links to Facebook accounts; and links to other apps. In addition, the information/data provided to the PED 440 promotes interaction of a user of the PED with the management platform 420 and brand/tag manager 430, thereby engaging the user and enhancing sales of products associated with the tags 400.

Turning now to FIG. 10, another embodiment of the system is shown generally at reference numeral 50. The system 50 includes an information tag printer 500 that is operable to print an information tag 502 onto a flexible pouch 504. In addition, the information tag is operable to receive and/or send information to a PED 506. A user of the PED 506 can make a selection 508 in response to the signal from the information tag 502 and the selection is communicated to the management platform 512 via a communication network 510. The selection may or may not be communicated to the brand/tag manager 514 and a response 516 is communicated via the communication network back to the PED 506. In this manner, the management platform 512 and/or brand/tag manager 514 can provide a customized response after viewing or analyzing the selection 508. In addition, based on the selections and/or responses, the management platform 512 can be in communication with a software unit 520 that is in communication with the printer 500 and be used to code future information tags 502.

Figure 11:
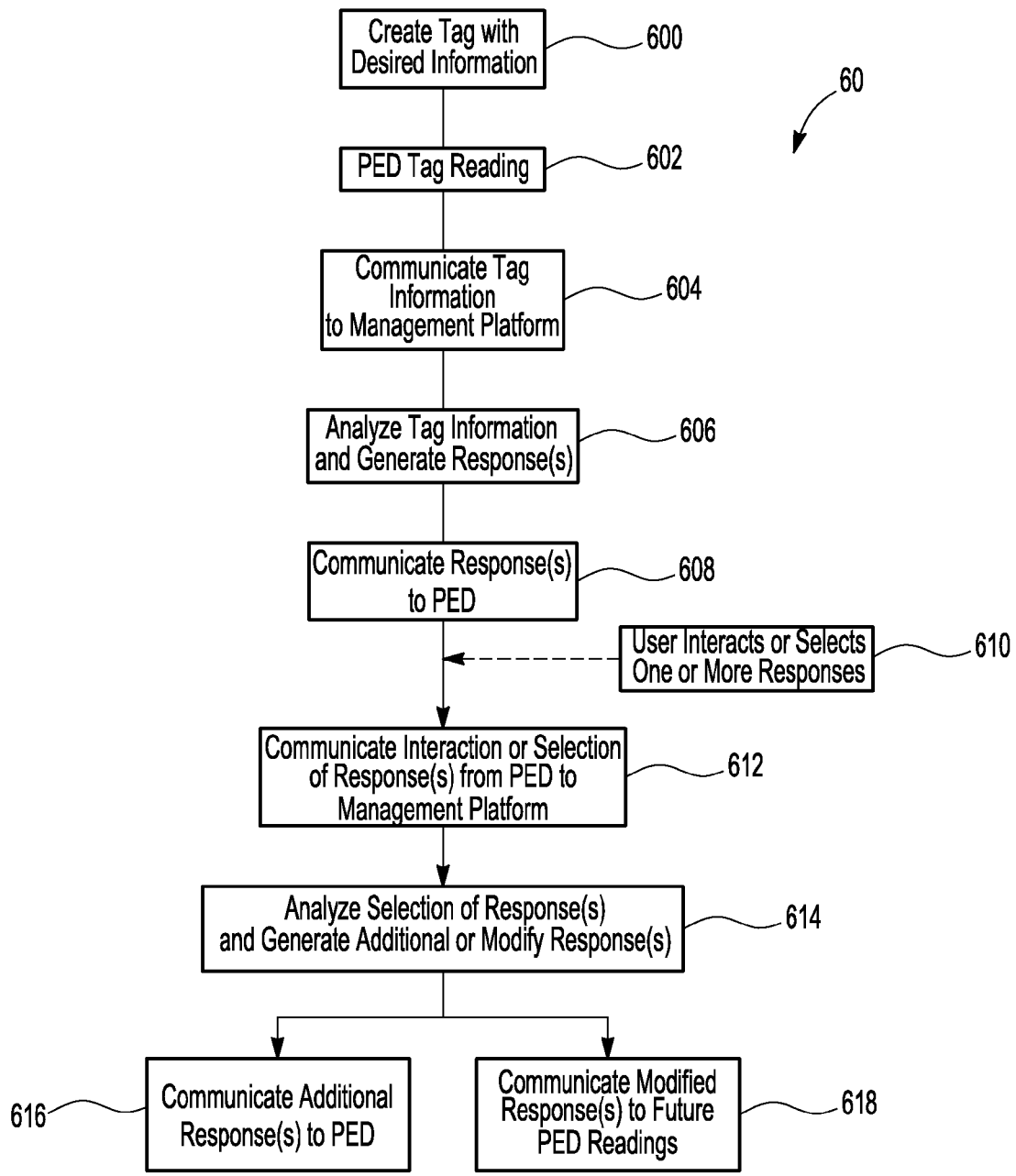
FIG. 11 is a schematic illustration of a system according to an embodiment of the present invention.

Referring to FIG. 11, a process according to an embodiment of the present invention is shown generally at reference numeral 60. The process 60 includes creating a tag with desired information at step 600 and reading the tag with a PED at step 602. The information read from the tag at step 602 is communicated with a management platform at step 604. The tag information is analyzed and one or more responses is generated at step 606. The response or responses are communicated to the PED at step 608 and a user may or may not interact or select one or more of the responses at step 610. The interaction or selection of the one or more responses from the PED is communicated back to the management platform at step 612. The management platform analyzes the selection of the one or more responses and generates additional responses and/or modifies future responses at step 614. At step 616 an additional one or more responses is communicated back to the PED, while at step 618 one or more modified responses are generated by the management platform to be used at step 608 in the future. This cycle can be repeated such that continued interaction and analysis of responses provided by one or more users of the PED are analyzed and used to provide desired information to the users, and also provide valuable marketing information to businesses, retailers and the like.

The invention is not to be limited to the described embodiments herein, but it should be appreciated that one skilled in the art would make various changes, modifications, etc. and still fall within the scope of the invention. It is the claims, including all equivalents, that define the scope of the invention.

We claim:

1. A system for obtaining Information from flexible pouches comprising:
   a flexible pouch with a Near Field Communicator (NFC) tag;
   a communication network;
   a management platform and a brand/tag manager in communication with said communication network; and
   a personal electronic device (PED) operable to read said NFC tag, provide said management platform with information read from said tag and receive a response from at least one of said management platform and said brand/tag manager;
   said PEP operable to receive said at least one response, generate a reply provided by a user and communicate said reply to at least one of said management platform and said brand/tag manager via said communication, network;
   said management platform operable to receive said reply from said FED, execute a past, present, and ongoing analysis of replies provided by a plurality of users with PEDs that have read a plurality of NFC tags on a plurality of flexible pouches, and modify future responses as a function of said analysis.

2. The system of claim 1, wherein said NFC tag has at least one type of information selected from the group consisting of nutritional information on a product within said flexible pouch, marketing information on said product within said flexible pouch, marketing information on said flexible pouch, an age restriction for a purchaser of said flexible pouch, a URL address, a unique flexible pouch ID, a unique ID for a set of flexible pouches, a time and date of manufacture of said flexible pouch, a content within said flexible pouch, a manufacturer of said flexible pouch, a manufacturer of said content within said flexible pouch and a time and a date when said content was placed within said flexible pouch.

3. The system of claim 2, wherein at least one of said management platform and said brand/tag manager responds to said information read from said NFC tag and provided by said PED with at least one response, said at least one response selected from the group consisting of a sales coupon, an advertisement, a question, a link to an electronic game, an electronic game download, a photograph a song, a recall notice for said content within said flexible pouch, a dosage chart for said content within said flexible pouch, medication indication information for said content within said flexible pouch and medication contraindication information for said content within said flexible pouch.

4. The system of claim 3, wherein said management platform provides said at least one response to said PED via said communication network.

5. The system of claim 3, wherein said brand/tag manager provides said at least one response to said PED via said management platform and said communication network.

6. The system of claim 2, further comprising said PED operable to provide at least one of a location of said PED when said PED reads said NFC tag, a time when said PED reads said NFC tag and a date when said PED reads said NFC tag to said management platform, wherein said management platform is operable to modify future responses as a function of said at least one of said location of said PED when said PED reads said NFC tag, said time when said PED reads said NFC tag and said date when said PED reads said NFC tag.

7. The system of claim 6, wherein said NFC tag has an antenna printed onto said flexible pouch.

8. The system of claim 7, wherein said antenna is printed onto said flexible pouch with an information tag printer.

9. The system of claim 8, wherein said antenna is printed with said information tag printer with an ink containing conductive nanoparticles.

10. The system of claim 9, further comprising a software unit operable to code said NFC tag with said at least one type of information during printing of said NFC tag.

11. The system of claim 10, wherein said software unit is located on at least one of a flexible pouch manufacturing machine and said information tag printer, said software unit operable to code said NFC tag on the fly and as a function of said analysis.

12. A system for obtaining information from flexible pouches comprising:
   a flexible pouch manufacturing machine;
   a flexible pouch manufactured on said flexible pouch manufacturing machine;
   a Near Field Communicator (NFC) tag printed on said flexible poach with a printer on said flexible pouch manufacturing machine, said printer having an electronic control unit with a software module, said NFC tag coded with information by said software module;
   a communication network;
   a management platform and a brand/tag manager in communication with said communication network and said printer software module: and
   a personal electronic device (PED) operable to read said NFC tag provide said management platform with said coded information read from said NFC tag and receive a response from at least one of said management platform and said brand/tag manager;
   said PED also operable to receive said response, generate a reply provided by a user and communicate said reply to at least one of said management platform and said, brand/tag manager via said communication network;

said management platform, operable to execute a past, present and ongoing analysis of replies provided by a plurality of users with PEDs that have read a plurality of NFC tags on a plurality of flexible pouches, and modify future responses sent to said PED as a function of said analysis;

said software, module operable to code future NFC tags as a function of said analysis.

13. The system of claim 12, wherein said NFC tag has at least one type of information selected from the group consisting of nutritional information on a product within said flexible pouch, marketing information on said product within said flexible pouch, marketing information on said flexible pouch, an age restriction for a purchaser of said flexible pouch, a URL address, a unique flexible pouch ID, a unique ID for a set of flexible pouches, a time and date of manufacture of said flexible pouch, a content within said flexible pouch, a manufacturer of said flexible pouch, a manufacturer of said content within said flexible pouch and a time and a date when said content was placed within said flexible pouch.

14. The system of claim 13, wherein at least one of said management platform and said brand/tag manager responds to said information read from said NFC tag and provided by said PED with at least one response, said at least one response selected from the group consisting of a sales coupon, an advertisement, a question, a link to an electronic game, an electronic game download, a photograph a song, a recall notice for said content within said flexible pouch, a dosage chart for said content within said flexible pouch, medication indication information for said content within said flexible pouch and medication contraindication information for said content within said flexible pouch.

15. The system of claim 14, wherein said management platform provides said at least one response to said PED via said communication network.

16. The system of claim 15, wherein said brand/tag manager provides said at least one response to said PED via said management platform and said communication network.

17. The system of claim 16, wherein said PED is operable to receive said at least one response, generate a reply provided by a user and communicate said reply to at least one of said management platform and said brand/tag manager via said communication network.

18. The system of claim 17, wherein said management platform executes an analysis of said reply and modifies at least one future response as a function of said analysis.

* * * * *